(12) United States Patent
Mori et al.

(10) Patent No.: US 9,200,269 B2
(45) Date of Patent: Dec. 1, 2015

(54) β-GLUCURONIDASE INHIBITOR (75) Inventors: Ichiro Mori, Tokyo (JP); Shunichi Akiba, Tokyo (JP)

(73) Assignee: KAO CORPORATION, Tokyo (JP)

( * ) Notice: Subject to any disclaimer, the term of this patent is extended or adjusted under 35 U.S.C. 154(b) by 443 days.

(21) Appl. No.: 12/679,244

(22) PCT Filed: Sep. 19, 2008

(86) PCT No.: PCT/JP2008/002602
§ 371 (c)(1),
(2), (4) Date: Mar. 19, 2010

(87) PCT Pub. No.: WO2009/037861
PCT Pub. Date: Mar. 26, 2009

(65) Prior Publication Data
US 2010/0247475 A1 Sep. 30, 2010

(30) Foreign Application Priority Data
Sep. 20, 2007 (JP) ................. 2007-243661

(51) Int. Cl.
*A61L 9/01* (2006.01)
*C12N 9/99* (2006.01)
*A61K 8/35* (2006.01)
*A61K 8/49* (2006.01)
*A61Q 15/00* (2006.01)

(52) U.S. Cl.
CPC ... *C12N 9/99* (2013.01); *A61K 8/35* (2013.01); *A61K 8/4973* (2013.01); *A61Q 15/00* (2013.01); *A61K 2800/782* (2013.01)

(58) Field of Classification Search
CPC . A61K 8/35; A61K 8/4973; A61K 2800/782; C12N 9/99; A61Q 15/00
See application file for complete search history.

(56) References Cited

U.S. PATENT DOCUMENTS

| | | | |
|---|---|---|---|
| 4,840,792 A | 6/1989 | Joulain et al. | |
| 5,447,719 A | 9/1995 | Kamataki | |
| 6,379,658 B1 * | 4/2002 | Marano et al. | 424/65 |
| 8,093,203 B2 * | 1/2012 | Yamamoto et al. | 512/8 |
| 2002/0123437 A1 * | 9/2002 | Conboy et al. | 510/101 |
| 2003/0152538 A1 * | 8/2003 | Preti et al. | 424/65 |
| 2003/0175395 A1 | 9/2003 | Starkenmann | |
| 2004/0223871 A1 * | 11/2004 | Woo et al. | 422/5 |
| 2007/0149424 A1 * | 6/2007 | Warr et al. | 510/101 |
| 2007/0197471 A1 | 8/2007 | Ichikawa | |

FOREIGN PATENT DOCUMENTS

| | | | |
|---|---|---|---|
| EP | 0 958 833 | 11/1999 | |
| GB | WO2004/098666 | * 11/2004 | ............. A61L 15/46 |
| JP | 1-501041 | 4/1989 | |
| JP | 5 43469 | 2/1993 | |
| JP | 5 137774 | 6/1993 | |
| JP | 07-047108 | 2/1995 | |
| JP | 08-019595 | 1/1996 | |
| JP | 9 30944 | 2/1997 | |
| JP | 2002 255776 | 9/2002 | |
| JP | 2003 501384 | 1/2003 | |
| JP | 2003-183697 A | 7/2003 | |
| JP | 2003-321698 | 11/2003 | |
| JP | 2004 91338 | 3/2004 | |
| JP | 2004-180979 | 7/2004 | |
| JP | 2005-65750 A | 3/2005 | |
| JP | 2006 45188 | 2/2006 | |
| JP | 2006-149893 | 6/2006 | |
| JP | 2006 192127 | 7/2006 | |
| JP | 2006 255290 | 9/2006 | |
| JP | 2007-029175 | 2/2007 | |
| JP | 2007 176868 | 7/2007 | |
| JP | 2007 518814 | 7/2007 | |
| JP | 2008-173441 | 7/2008 | |
| WO | WO 2004/098666 A1 | 11/2004 | |
| WO | WO2006/051597 | * 5/2006 | ................ C11B 9/00 |

OTHER PUBLICATIONS

C. Froebe, et al, Axillary Malodor Production: A New Mechanism, 41 J Soc. Cosmet. Chem. 173 (1990).*
Bruce Keswick, et al, Diaper Area Skin Microflora of Normal children and Children with Atopic Dermatitis, 25 J Clin. Microbiol. 216 (1987).*
European Search Report issued Sep. 28, 2010, in European Patent Office Application No. 08831650.0 2404 / 2192178 PCT/JP2008002602.
The RIFM Expert Panel, D. Belsito, et al., "A toxicologic and dermatologic assessment of ionones when used as fragrance ingredients", Food and Chemical Toxicology 45, Science Direct, (Elsevier), XP 022372913, Jan. 1, 2007, pp. S130-S167.
Axel, "Scents and Sensibility: A Molecular Logic of Olfactory Perception" Nobel Lecture, Dec. 2004.
Buck et al, A novel multigene family may encode odorant receptors: a molecular basis for odor recognition *Cell*, 1991 vol. 65, pp. 175-187.

* cited by examiner

*Primary Examiner* — Sean Basquill
(74) *Attorney, Agent, or Firm* — Oblon, McClelland, Maier & Neustadt, L.L.P.

(57) ABSTRACT

Provided are a novel β-glucuronidase inhibitor including a compound selected from a macrocyclic ketone, a ketone, a macrocyclic lactone, a macrocyclic oxalactone, an ester, an aldehyde, an alcohol, and a terpene of specific kinds, and an environmental hygiene product and a sanitary product each containing the β-glucuronidase inhibitor. Also provided are a composition for suppressing the generation of urine odor and a method of suppressing the generation of urine odor each using a β-glucuronidase inhibitor.

9 Claims, 2 Drawing Sheets

β-GLUCURONIDASE INHIBITOR

CROSS REFERENCE TO RELATED APPLICATION

This application is a 371 of PCT/JP08/002602, filed on Sep. 19, 2008, and claims priority to Japanese Patent Application No. 2007-243661, filed on Sep. 20, 2007.

FIELD OF THE INVENTION

The present invention relates to a β-glucuronidase inhibitor, and a composition for suppressing the generation of urine odor.

BACKGROUND OF THE INVENTION

In recent years, along with increasing hygiene consciousness amongst consumers, there is a strong demand for removing not only a dirty appearance but also odor that reminds us of the presence of dirt. In particular, the presence of urine and stools cannot be shut off from a living environment. In addition, the odor thereof strongly reminds us of the excreta themselves, and hence gives unpleasant feeling to a human, the extent of which is particularly large among offensive odor from a living environment. In a toilet, stools are easily exhausted from the room by water washing, while a small amount of urine remains as a droplet outside of a toilet bowl and stays on the site for a long period of time because of the difficulty of a visual check for its presence. Thus, the toilet has a tendency to become a source of offensive odor. Further, sanitary products, such as underwear, a diaper, and a menstrual hygiene product, to which urine being deposited, may also exist in a living environment for a given period, and thus may become a source of offensive odor derived from urine.

It is known that urine itself generally generates no unpleasant odor, and generate unpleasant odor through activities of a microorganism. An example of the unpleasant odor includes ammonia resulting from decomposition of urea with urease, and the inhibition of the generation of urine odor (ammonia odor) by using urease inhibitor has been proposed (for example, see Patent Documents 1 to 4).

However, ammonia is a component of offensive order having a high threshold (i.e. the odor is sensed only at high concentrations), and therefore, ammonia odor is rarely strongly sensed at present when excreta are instantaneously exhausted from the room owing to spread of a water washing system.

Meanwhile, a β-glucuronidase is an enzyme that hydrolyzes compounds prepared by glucuronidation of various alcohols, phenols, amines and the like (glucuronides), and exists in many living organisms such as bacteria, fungi, plants and animals. For example, it is known that glucuronides secreted into a human sweat are involved in the production of substances that generate axillary odor through metabolism of a bacterium living in the skin (Patent Document 5). However, the relation between the enzyme and the urine odor has not been known.

[Patent Document 1] JP-A-2006-255290
[Patent Document 2] JP-A-2004-91338
[Patent Document 3] JP-05-137774
[Patent Document 4] JP-A-2006-192127
[Patent Document 5] JP-A-2002-255776

SUMMARY OF THE INVENTION

The present invention provides a β-glucuronidase inhibitor, including a macrocyclic ketone represented by the formula (1):

wherein $n_1$ represents an integer of 9 to 13; $m_1$ represents an integer of 0 to 2; and a dashed line portion may include one double bond.

In addition, the present invention provides a β-glucuronidase inhibitor, including a ketone selected from cyclopentadecanone, 3-methylcyclopentadecanone, 3-methyl-4(5)-cyclopentadecen-1-one, 4-cyclopentadecen-1-one, 5-cyclohexadecen-1-one, 8-cyclohexadecen-1-one, 9-cycloheptadecen-1-one, 2-pentylcyclopentenone, α-damascone, β-damascone, cis-jasmone, 2-heptylcyclopentanone, α-ionone, β-ionone, α-methylionone, γ-methylionone, 7-methyl-3,4-dihydro-(2H)-1,5-benzodioxepin-3-one, nootkatone, and 1,2,3,4,5,6,7,8-octahydro-2,3,8,8-tetramethyl-2-acetonaphthone In addition, the present invention provides a β-glucuronidase inhibitor, including a macrocyclic lactone represented by the following formula (2):

wherein $n_2$ represents an integer of 9 to 13; $m_2$ represents an integer of 0 to 3; and a dashed line portion includes one double bond; provided that $n_2+m_2=9$ to 14.

In addition, the present invention provides a β-glucuronidase inhibitor, including a macrocyclic oxalactone represented by the following formula (3):

wherein R represents a hydrogen atom or an alkyl group having 1 to 3 carbon atoms; p represents an integer of 6 to 11; and q represents an integer of 2 to 6; provided that $p+q=10$ to 14.

In addition, the present invention provides a β-glucuronidase inhibitor, including an ester selected from 4(5)-cyclopentadecenolide, 7-cyclohexadecenolide, 10-oxa-16-hexadecanolide, 11-oxa-16-hexadecanolide, citronellyl acetate, linalyl acetate, terpinyl acetate, cinnamyl acetate, cis-3-hexenyl benzoate, and methyl-2-nonynoate.

In addition, the present invention provides a β-glucuronidase inhibitor, including an aldehyde selected from anisaldehyde, cinnamic aldehyde, cuminaldehyde, cyclamen aldehyde, ethylvanillin, 2-methyl-3-(3,4-methylenedioxyphenyl)-propanal, 2-methyl-3-(4-tert-butylphenyl)-propanal, phenylacetaldehyde, 3-phenylpropanal, vanillin, 4-(tricyclo[5.2.1.0$^{2,6}$]decylidene-8)butenal, dimethyltetrahydrobenzaldehyde, 4-(4-hydroxy-4-methylpentyl)-3-cyclohexene-1-carboxyaldehyde, 4-(4-methyl-3- pentenyl)-3-cyclohexene-1-carboxyaldehyde, 2,6-nonadienal, 2-methylundecanal, hydroxycitronellal, and citral.

In addition, the present invention provides a β-glucuronidase inhibitor, including an alcohol selected from citronellol, geraniol, nerol, linalool, linalool oxide, terpineol, cinnamic alcohol, eugenol, 3-methyl-5-phenyl-1-pentanol, and vetiverol.

In addition, the present invention provides a β-glucuronidase inhibitor, including an ether selected from estragole, 6,6,9α-trimethyl-3α-ethyldodecahydronaphtho[2,1-b]furan, p-cresyl methyl ether, phenylethyl isoamyl ether, 1-methoxycyclododecane, 1-methyl-1-methoxycyclododecane, and 4,8,12-trimethyl-13-oxabicyclo-[10.1.0]trideca-4,8-diene.

In addition, the present invention provides a β-glucuronidase inhibitor, including a terpene selected from α-phellandrene and citronellyl nitrile.

In addition, the present invention provides a use of the above-mentioned β-glucuronidase inhibitor including a macrocyclic ketone, a ketone, a macrocyclic lactone, a macrocyclic oxalactone, an ester, an aldehyde, an alcohol, an ether, and a terpene, and a method of inhibiting a β-glucuronidase.

In addition, the present invention provides an environmental hygiene product and a sanitary product, each including the above-mentioned novel β-glucuronidase inhibitor.

In addition, the present invention provides a composition for suppressing the generation of urine odor containing a β-glucuronidase inhibitor (not being limited to each of the above-mentioned β-glucuronidase inhibitors and including the other various kinds of substances inhibiting β-glucuronidase activity) as an active ingredient. Further, the present invention provides a method of suppressing the generation of urine odor by inhibition of a β-glucuronidase activity, and a method of suppressing the generation of urine odor including application of β-glucuronidase inhibitor inhibiting β-glucuronidase activity is applied to an object before urine is deposited to the object or before urine is dried after having been deposited to the object.

DETAILED DESCRIPTION OF THE INVENTION

The inventors of the present invention have found that phenol-based compounds and indoles generated from urine are main components of urine odor, and these components are remarkably increased by β-glucuronidase activity to urine derived from a microbial cell. Further, in a current living environment in which excreta are instantaneously exhausted from the room, strong ammonia odor is rarely sensed, and thus, urine odor generally sensed by consumers is thought to be derived from the above-mentioned phenol-based compounds and indoles each having a lower threshold than that of from ammonia, as offensive odor components.

Then, the inventors have found that a β-glucuronidase inhibitor can actually continuously suppress the increase of phenol-based compounds and indoles in urine and the generation of unpleasant urine odor, and can be used for products associated with urine to impart an effect of suppressing the generation of urine odor on those products. In addition, the inventors have found that a compound chosen from a specific group has an excellent β-glucuronidase inhibitory effect.

The β-glucuronidase inhibitor of the present invention can continuously suppress the generation of an offensive odor component that characterizes urine odor, and hence is useful for an environmental hygiene product, each having an excellent deodorization effect, and sanitary products such as a diaper such as a detergent and a deodorant, a menstrual hygiene product, and animal excreta-related products such as a sheet for excreta of pets such as dog and cat. Further, the β-glucuronidase inhibitor of the present invention may also be used as means for solving various problems other than urine odor due to β-glucuronidase activity, for example, as an agent for suppressing the generation of body odor derived from a volatile steroid, and as a medicament or a food for reducing the development of bladder cancer or large bowel cancer.

[β-Glucuronidase Inhibitor]

The β-glucuronidase refers to an enzyme that hydrolyzes compounds prepared by glucuronidation of various alcohols, phenols, amines and the like (glucuronides), and exists in many living organisms such as bacteria, fungi, plants, and animals. Microorganisms are highly involved in the decomposition of urine excreted from the body. Therefore, β-glucuronidases derived from bacteria and fungi are important for the present invention. Specific examples thereof include β-glucuronidases derived from *Escherichia coli, Lactobacillus brevis, Propionibacterium acnes, Clostridium perfringens, Staphylococcus haemolyticus, Streptococcus agalactiae, Streptococcus pyogenes, Haemophilus somunus, Shigela sonnei*, and *Aspergillus niger*. The β-glucuronidases from those microorganisms are classified into enzymes having a common domain. In addition, a β-glucuronidase derived from human plasma is also classified into a similar protein family.

The β-glucuronidase inhibitor used in the present invention refers to an inhibitor which have been demonstrated to suppress 60% or more of β-glucuronidase Type VII-A activity of 1.6 units/mL derived from *Escherichia coli* when 0.1 wt % amount of the inhibitor is added to a reaction solution. In addition, the inhibitor that suppresses 80% or more of the above-mentioned activity when 0.01 wt % amount of the inhibitor is added to a reaction solution, is preferably used.

Of the β-glucuronidase inhibitors defined as described above, novel β-glucuronidase inhibitors that have been found out in the present invention are listed below.

1. A Macrocyclic Ketone Represented by the Following Formula (1):

wherein $n_1$ represents an integer of 9 to 13; $m_1$ represents an integer of 0 to 2; and a dashed line portion may include one double bond.

Examples thereof include 3-methyl-4(5)-cyclopentadecen-1-one (Firmenich, Inc. product name; Muscenone delta), 3-methylcyclopentadecanone (Firmenich, Inc. product name; Muscone), 4-cyclopentadecen-1-one (Firmenich, Inc. product name; Exaltenone, International Flavors & Fragrances Inc. product name: Musk Z-4), 5-cyclohexadecen-1-one (Soda Aromatic Co., Ltd. product name; Musk TM2), 8-cyclohexadecen-1-one (Symrise AG product name; Globanone), 9-cycloheptadecen-1-one (Firmenich, Inc. product name; Civetone), and cyclopentadecanone (Firmenich, Inc. product name; Exaltone).

Of macrocyclic ketone compounds represented by the formula (1), a compound including one double bond in a cyclic structure is preferred, and examples thereof include 3-methyl-4(5)-cyclopentadecen-1-one, 4-cyclopentadecen-1-one, 5-cyclohexadecen-1-one, 8-cyclohexadecen-1-one, and 9-cycloheptadecen-1-one. In addition, the double bond preferably exists in a carbon-carbon bond at the most distant position from a carbonyl group in the ketone, or a carbon-carbon bond adjacent thereto, and for example, 8-cyclohexadecen-1-one and 9-cycloheptadecen-1-one are preferred. Further, in the formula (1), $n_1+m_1$ preferably represents 9 to 13 and $n_1$ preferably represents 11 or 12.

2. A Macrocyclic Lactone Represented by the Following Formula (2):

(2)

wherein $n_2$ represents an integer of 9 to 13; $m_2$ represents an integer of 0 to 3; and a dashed line portion includes one double bond; provided that $n_2+m_2=9$ to 14.

Examples thereof include 4(5)-cyclopentadecenolide (Firmenich, Inc. product name: Habanolide) and 7-cyclohexadecenolide (Ambrettolide). As the macrocyclic lactone compound represented by the formula (2), preferred is a compound wherein $n_2$ represents 12, and more preferred is 7-cyclohexadecenolide.

3. A Macrocyclic Oxalactone Represented by the Following Formula (3):

(3)

wherein R represents a hydrogen atom or an alkyl group having 1 to 3 carbon atoms; p represents an integer of 6 to 11; and q represents an integer of 2 to 6; provided that p+q=10 to 14.

Examples thereof include 10-oxa-16-hexadecanolide (Takasago International Corporation product name; Oxalide), 11-oxa-16-hexadecanolide (Quest International product name; Musk R1), and 12-oxa-16-hexadecanolide (Quest International product name; Cervolide). As the macrocyclic oxalactone compound represented by the formula (3), preferred is a compound in which p+q represents 13, and more preferred is 10-oxa-16-hexadecanolide.

4. Ketones:

cyclopentadecanone (Firmenich, Inc. product name; Exaltone), 3-methylcyclopentadecanone (Firmenich, Inc. product name; Muscone), 3-methyl-4(5)-cyclopentadecen-1-one (Firmenich, Inc. product name; Muscenone delta), 4-cyclopentadecen-1-one (Firmenich, Inc. product name; Exaltenone, International Flavors & Fragrances Inc. product name: Musk Z-4), 5-cyclohexadecen-1-one (Soda Aromatic Co., Ltd. product name; Musk TM2), 8-cyclohexadecen-1-one (Symrise AG product name; Globanone), 9-cycloheptadecen-1-one (Firmenich, Inc. product name; Civetone), 2-pentylcyclopentenone, α-damascone, β-damascone, cis-jasmone, 2-heptylcyclopentanone, α-ionone, β-ionone, α-methylionone, γ-methylionone, 7-methyl-3,4-dihydro-(2H)-1,5-benzodioxepin-3-one (Danisco A/S product name: Calone), nootkatone, and 1,2,3,4,5,6,7,8-octahydro-2,3,8,8-tetramethyl-2-acetonaphthone (International Flavors & Fragrances Inc. product name: IsoE Super).

5. Esters:

4(5)-cyclopentadecenolide (Firmenich, Inc. product name: Habanolide), 7-cyclohexadecenolide (Ambrettolide), 10-oxa-16-hexadecanolide (Takasago International Corporation product name; Oxalide), 11-oxa-16-hexadecanolide (Quest International product name; Musk R1), citronellyl acetate, linalyl acetate, terpinylacetate, cinnamylacetate, cis-3-hexenylbenzoate, and methyl-2-nonynoate (trivial name: methyl octine carbonate).

6. Aldehydes:

anisaldehyde, cinnamic aldehyde, cuminaldehyde, cyclamen aldehyde, ethylvanillin, 2-methyl-3-(3,4-methylenedioxyphenyl)-propanal (International Flavors & Fragrances Inc. product name: Helional), 2-methyl-3-(4-tert-butylphenyl)-propanal (Givaudan S. A. product name; Lilial), phenylacetaldehyde, 3-phenylpropanal, vanillin, 4-(tricyclo[5.2.1.0$^{2,6}$]decylidene-8)butenal (International Flavors & Fragrances Inc. product name: Dupical), dimethyltetrahydrobenzaldehyde (International Flavors & Fragrances Inc. product name: Triplal, Quest International product name; Ligustral), 4-(4-hydroxy-4-methylpentyl)-3-cyclohexene-1-carboxyaldehyde (International Flavors & Fragrances Inc. product name: Lyral), 4-(4-methyl-3-pentenyl)-3-cyclohexene-1-carboxyaldehyde (International Flavors & Fragrances Inc. product name: Myrac Aldehyde), 2,6-nonadienal, 2-methylundecanal, hydroxycitronellal, and citral.

7. Alcohols:

citronellol, geraniol, nerol, linalool, linalool oxide, terpineol, cinnamic alcohol, eugenol, 3-methyl-5-phenyl-1-pentanol (Firmenich, Inc. product name; Phenylhexanol), and vetiverol.

8. Ethers:

estragole, 6,6,9α-trimethyl-3α-ethyldodecahydronaphtho[2,1-b]furan (International Flavors & Fragrances Inc. product name: Grisalva), p-cresyl methyl ether, phenylethyl isoamyl ether, 1-methoxycyclododecane (Symrise AG product name; Palisandin), 1-methyl-1-methoxycyclododecane (Givaudan S. A. product name; Madrox), and 4,8,12-trimethyl-13-oxabicyclo-[10.1.0]trideca-4,8-diene (Firmenich, Inc. product name; Cedroxyde).

9. Terpenes:

α-phellandrene and citronellyl nitrile.

The above-mentioned novel β-glucuronidase inhibitor may be used as isolated product from plants or animals, or as chemically synthesized product. Further, plant extracts including essential oils containing those compounds, such as vetiver oil, basil oil, clove oil, cinnamon oil and grapefruit oil, may be directly used as the β-glucuronidase inhibitor. Those compounds or plant extracts may be used as a combination of two or more thereof.

In the composition for suppressing the generation of urine odor and the method of suppressing the generation of urine odor of the present invention, the β-glucuronidase inhibitor is not limited to the above-mentioned novel β-glucuronidase inhibitor of the present invention as long as the β-glucuronidase inhibitor has such β-glucuronidase inhibitory activity as mentioned above, and any known β-glucuronidase inhibitor may also be used.

Examples thereof known for inhibiting β-glucuronidase activity include: D-glucaro-1,4-lactone which are lactone compounds derived from glucronic acid, and its analogs such as aceglatone, D-glucuronic acid, and D-galacturonic acid; lysophospholipids such as lysophosphatidic acid, lysophosphatidylcholine, lysophosphatidylethanolamine, and lysophosphatidylglycerol; natural glucuronic acid conjugates found in herbal medicine components such as baicalin; and plants or fungi inhibiting β-glucuronidase activity such as *Scutellariae radix*, *Galla rhois*, *Syzygium aromaticum*, *Gardenia jasminoides*, *Lithospermum erythrorhizon*, *Paeonia lactiflora*, *Rabdosia japonica*, *Matricaria recutita*, *Centella asiatica*, *Symphytum officinale*, *Hydrangea macrophylla* var. *thunbergii*, *Glycyrrhiza*, *Swertia japonica*, *Cordyceps sinensis*, *Citrus unshiu*, *Urtica thunbergiana*, and *Hamamelis virginiana*, or extracts thereof.

For the above-mentioned plants and microbes, one or more of whole herbs, leaves, roots, rhizomes, fruits, seeds, and flowers of the plants, and the microbes may be used directly or after grinding. When an extract are used, the extract may be prepared by extraction from the above-mentioned plants or microbes or ground products thereof with a solvent at a normal temperature or under heating. The extraction may also be performed with an extraction apparatus such as a Soxhlet extraction apparatus.

Examples of the solvent used for extraction include: water; alcohols such as methanol, ethanol, and propanol; polyalcohols such as propylene glycol and butylene glycol; ketones such as acetone and methyl ethyl ketone; esters such as methyl acetate and ethyl acetate; linear and cyclic ethers such as tetrahydrofuran and dimethyl ether; hydrogen halides such as dichloromethane, chloroform, and carbon tetrachloride; hydrocarbons such as hexane, cyclohexane, and petroleum ether; aromatic hydrocarbons such as benzene and toluene; polyethers such as polyethylene glycol; and pyridines. Those solvents may be used alone or as a mixture. In addition, supercritical fluids, such as carbon dioxide, may be used.

The prepared various solvent extracts may be directly used, may be used as diluted or concentrated preparation, or may be prepared as concentrated or lyophilized preparation and then used as a powder or a paste. Further, with use of a technology such as liquid-liquid distribution, an inactive contaminant may be removed from the above-mentioned extract before use, and in the present invention, such technology is preferably used. When required, those may be subjected to an operation such as deodorization and decolorization by a known method before use.

[Composition for Suppressing Generation of Urine Odor, Method Of Suppressing Generation of Urine Odor, Environmental Hygiene Product, and Sanitary Product]

In the present invention, the above-mentioned β-glucuronidase inhibitors may be incorporated into the composition alone or combination of two or more thereof for suppressing the generation of urine odor. Further, the β-glucuronidase inhibitor or the composition for suppressing the generation of urine odor of the present invention may be incorporated into an environmental hygiene product or a sanitary product, for example, for family or facility use in an effective amount, in order to produce a product having high suppression and deodorization effects on the generation of offensive odor derived from urine. Further, the β-glucuronidase inhibitor may be applied to an object (an object in which the generation of urine odor should be suppressed) before urine is deposited to the object or before the deposited urine is dried after urine has been deposited to the object, or preferably within 1 hour or more preferably within 10 minutes after urine has been deposited, to thereby suppress the generation of urine odor effectively.

The above-mentioned urine is not limited to urine derived from a human, and may be derived from animals such as pets, typically dog or cat. Further, the above-mentioned offensive odor derived from urine is not limited to offensive odor generated from urine alone, but it may be, for example, offensive odor generated from such a condition that urine and stools have been mixed in a diaper or the like.

Examples of the offensive odor component which may be controlled by the β-glucuronidase inhibitor of the present invention include phenol-based compounds and indoles. Specific examples thereof include, but not limited to, phenol, p-cresol, 4-vinyl-2-methoxy-phenol, 4-vinylphenol, 2-methoxy-1,3-benzenediol, 1,4-benzenediol, 1,3-benzenediol, and indole, and any volatile component produced by β-glucuronidase activity on urine may be controlled.

The content of the β-glucuronidase inhibitor in the composition for suppressing the generation of urine odor of the present invention is preferably 0.0001 to 5 wt %, more preferably 0.001 to 1 wt %, and still more preferably 0.005 to 0.5 wt %.

(Environmental Hygiene Product)

Examples of the environmental hygiene product include a detergent, a deodorant, a textile detergent, and a wiping sheet. Further, several method may be used in combination. The environmental hygiene product of the present invention may be applied to places where offensive odor derived from urine is easily generated such as a toilet floor surface, a wall surface, a toilet bowl, a sanitary container, an inside of a nursing-care facility, clothes, underwear, and bedclothes, to thereby control the generation of urine odor.

The composition for suppressing the generation of urine odor used for the environmental hygiene product of the present invention may be optionally combined with, various generally used components, such as an oil, a surfactant, alcohols, a chelating agent, a pH adjustor, a microbicide, an antimicrobial agent, a preservative, a thickener, pigments, and a flavor, as well as a deodorant base, a humectant, a softener, a skin protectant, a medicinal agent, an antioxidant, a solvent, a metal salt, and a metal ion, in such a range of amount that an effect of the present invention is not inhibited, in order to prepare a formulation.

(Sanitary Product)

Examples of the sanitary product include absorbent products such as products for light urinary incontinence, a disposable paper diaper, a urine collection pad, and a menstrual hygiene product. The sanitary product of the present invention can control the time-dependent generation of offensive odor derived from urine from the deposited urine.

When being used for an absorbent product, the β-glucuronidase inhibitor or the composition for suppressing the generation of urine odor of the present invention is preferably impregnated in ground paper or an absorption layer, or in particular, a water-absorbent polymer. The impregnation amount of the β-glucuronidase inhibitor is preferably 0.005 to 10 g/m² and more preferably 0.05 to 2 g/m² with respect to an applied surface.

The composition for suppressing the generation of urine odor used for the sanitary product of the present invention may be optionally combined with generally used various components, such as an oil, a surfactant, an antistatic agent, an antioxidant, a pH adjustor, a lubricating agent, an antimicrobial agent, a fungicide, a preservative, pigments, and a flavor, as well as a deodorant base, a medicinal agent, a solvent, a metal salt, and a metal ion in such a range of amount that an effect of the present invention is not inhibited.

(Deodorant Base)

When the β-glucuronidase inhibitor or the composition for suppressing the generation of urine odor containing the β-glucuronidase inhibitor of the present invention is used for an environmental hygiene product or a sanitary product, a generally known deodorant base may be used in combination or may be incorporated in such a range of amount that a β-glucuronidase inhibition is not impaired.

Examples of the above-mentioned deodorant base include:

metal compounds such as iron oxide, iron sulfate, iron chloride, zinc oxide, zinc sulfate, zinc chloride, silver oxide, and copper oxide;

acids having a pH buffering effect, including a combination of an acid such as phosphoric acid, citric acid, and succinic acid, and a base such as triethanolamine, monoethanolamine, sodium hydroxide, potassium hydroxide, and 2-amino-2-hydroxymethyl-1,3-propanediol (tris(hydroxymethyl)aminomethane), or salts thereof;

carboxylic acids such as lactic acid, succinic acid, malic acid, citric acid, maleic acid, and malonic acid;

metal salts of fatty acids such as zinc undecylenate, zinc 2-ethylhexanoate, and zinc ricinoleate;

plant extract-based deodorants such as catechin, polyphenol, green tea extract, mushroom extract, pyroligneous acid, and bamboo pyroligneous acid;

catalyst-type deodorants such as sodium metal chlorophyllin such as sodium iron chlorophyllin and sodium copper chlorophyllin, metal phthalocyanine such as iron phthalocyanine, copper phthalocyanine, cobalt phthalocyanine, metal tetrasulfonated phthalocyanine such as iron tetrasulfonated-phthalocyanine, copper tetrasulfonated phthalocyanine, and cobalt tetrasulfonated phthalocyanine, titanium dioxide, and visible light responsive titanium dioxide (for example, nitrogen-doped type);

cyclodextrins such as α-, β-, or γ-cyclodextrine, and a methyl derivative, hydroxypropyl derivative, glucosyl derivative, and maltosyl derivative thereof;

alkylene glycols considered to have an effect of retaining offensive odor such as ethylene glycol, propylene glycol, diethylene glycol, and dipropylene glycol;

ester oils considered to have an effect of retaining offensive odor such as myristic acid esters, palmitic acid esters, phthalic acid esters, adipic acid esters, sebacic acid esters, and citric acid esters;

synthetic porous polymers including acrylic acid-based polymers such as a porous methacrylic acid polymer and a porous acrylic acid polymer, aromatic-based polymers such as a porous divinylbenzene polymer, a porous styrene-divinylbenzene-vinylpyridine polymer, and a porous divinylbenzene-vinylpyridine polymer, and copolymers thereof; and natural porous polymers such as chitin and chitosan;

inorganic porous substances such as activated carbon, silica, silicon dioxide (silica gel), calcium silicate, high-silica zeolite (hydrophobic zeolite), zepiolite, cancrinite, zeolite, and zirconium oxide hydrate; and metal-supported porous substances such as silver-supported zeolite, silver-supported cancrinite, and a silver-supported porous styrene-divinylbenzene-vinylpyridine polymer. Those deodorant bases may be used alone and, further, may be used in combination.

(Organic Solvent)

In addition, when the β-glucuronidase inhibitor or the composition for suppressing the generation of urine odor of the present invention is used for an environmental hygiene product or a sanitary product, a water-soluble organic solvent is preferable to be used in combination or incorporated.

Examples of the above-mentioned water-soluble organic solvent include:

alcohols such as ethanol, 1-propanol, 2-propanol, and butyl alcohol;

glycols such as ethylene glycol, 1,2-propanediol, 1,3-butanediol, hexylene glycol, 2-ethyl-1,3-hexanediol, glycerin, triethylene glycol, dipropylene glycol, diglycerin, polyethylene glycol, and polypropylene glycol; and ethers such as ethylene glycol ethyl ether, ethylene glycol methyl ether, ethylene glycol butyl ether, and diethylene glycol ethyl ether.

EXAMPLES

Reference Example 1

Production of Volatile Compound from Urine with Addition of β-Glucuronidase (1) Preparation of Sample for Measurement 9.9 mL of a human urine sample (a mixture of urine from five humans), from which microorganisms were filtered with a 0.2-μm filter (Millex GV manufactured by Millipore Corporation) were added to a bottle which had been preliminarily subjected to γ-ray sterilization immediately after the collection, and subsequently 0.1 mL of an *Escherichia coli*-derived β-glucuronidase Type VII-A (purchased from Sigma-Aldrich Corporation) aqueous solution adjusted to 250 units/mL was added and mixed. The mixture was incubated in a thermostat bath at 25° C. and allowed to react for 22 hours. An initial urine sample prepared by adding 0.1 mL of sterilized ion exchanged water as substitution of the enzyme solution, was similarly incubated in a thermostat bath for 22 hours.

After the completion of the reaction, to 9 mL of the reaction solution, a benzyl benzoate ethanol solution as an internal standard was added. The mixture was extracted twice with 10 mL of diethyl ether. The extracted solutions were combined and dried over anhydrous magnesium sulfate. After drying, a solid was separated by filtration, and the filtrate was concentrated with a rotary evaporator to prepare a measurement sample.

(2) Measurement of Volatile Compound

Measurement was performed with a gas chromatograph mass spectrometer. The produced amount of the volatile compound detected was calculated as a peak area ratio with respect to an internal standard. The results are shown in Table 1.

TABLE 1

| Volatile component | Initial urine (Peak area ratio) | Enzyme-added urine (Peak area ratio) |
|---|---|---|
| Phenol | 0.02 | 0.72 |
| p-Cresol | N.D. | 0.84 |
| 4-Vinyl-2-methoxyphenol | 0.03 | 0.21 |
| 4-Vinylphenol | 0.02 | 0.13 |
| 2-Methoxy-1,3-benzenediol | N.D. | 0.11 |
| 1,4-Benzenediol | N.D. | 0.28 |
| 1,3-Benzenediol | N.D. | 0.05 |
| Indole | 0.02 | 0.23 |

TABLE 1-continued

| Volatile component | Initial urine (Peak area ratio) | Enzyme-added urine (Peak area ratio) |
|---|---|---|

(N.D.: Not Detected)

According to the results, production of various phenol-based compounds and indole from urine by β-glucuronidase activity was confirmed.

Reference Example 2

Generation of Urine Odor Due to Addition of β-Glucuronidase (1) Preparation of Sample for Evaluation 360 μL of a human urine sample (a mixture of urine from five humans), from which microorganisms were filtered with a 0.2-μm filter immediately after the collection, were added to a bottle which had been γ-ray sterilized in advance, and subsequently 40 μL of a β-glucuronidase aqueous solution adjusted to 20 units/mL was added and mixed. The mixture was incubated in a thermostat bath at 25° C. and allowed to react for 2 hours. An initial urine sample, prepared by adding 40 μL of sterilized ion exchanged water as substitution of an enzyme solution, was similarly incubated in a thermostat bath for 2 hours. An equal amount of the each sample was dropped onto the tip of a smelling strip, and the strip was used as a sample for evaluation.

(2) Sensory Evaluation of Odor

Figure 1:
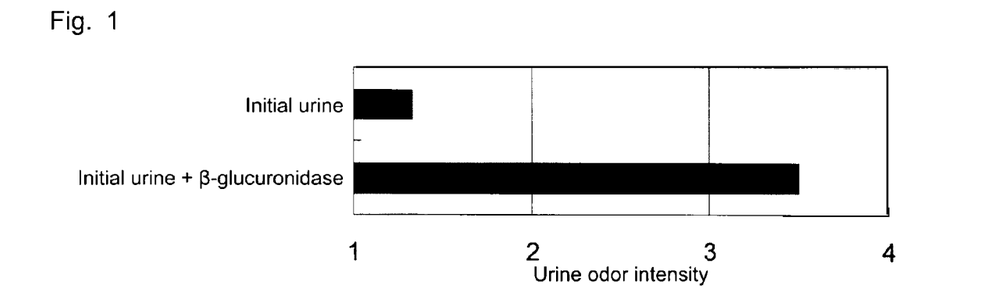
FIG. 1 Results of the sensory evaluation illustrating the increase of urine odor intensity by β-glucuronidase.

Sensory evaluation of odor was performed by six panelists, the evaluation was based on a six-level odor intensity indication method in which the odor intensity was indicated with an evaluation score of 0 to 5. In the evaluation score, "0" indicates no odor, "1" indicates odor which can be slightly perceived (detection threshold), "2" indicates odor which can be perceived to be urine odor but is weak (perception threshold), "3" indicates odor which can be easily perceived to be urine odor, "4" indicates strong urine odor, and "5" indicates extreme urine odor. The odor intensity was determined at an interval of 0.5. FIG. 1 shows the average values of the evaluation.

According to the results, remarkable increase of the urine odor intensity due to the volatile component produced by β-glucuronidase activity was confirmed.

Reference Example 3

Measurement of β-Glucuronidase Activity in Putrefied Urine (1) Preparation of sample A putrefied urine product, which was prepared by collecting 20 mL of a urine sample, dispensing the sample in a bottle which had been preliminarily subjected to γ-ray sterilization without performing any microbe removing operation and storing the resultant at room temperature for 7 days, was used. 1 mL of the putrefied urine was centrifuged at 10,000 rpm for 5 minutes, and separated into a microbial cell and a supernatant. The precipitated microbial cell was suspended in 0.5 mL of saline. The supernatant was subjected to sterilizing through a 0.2-μm filter.

Further, 15 mL of urine prepared by removing a microbe with a filter immediately after the collection were also similarly stored at room temperature for 7 days.

(2) Measurement of β-glucuronidase activity 250 μL of a 2 mM p-nitrophenyl-β-D-glucuronide (PNPG) aqueous solution, 100 μL of a 0.5 M phosphate buffer (pH 6.8) and 100 μL of ion exchanged water were mixed in a bottle γ-ray sterilized in advance, and subsequently 50 μL of the above-mentioned urine sample (microbe-removed urine, a putrefied urine microbial cell suspension or a putrefied urine supernatant) were added. Each mixture was allowed to react at room temperature.

Figure 2:
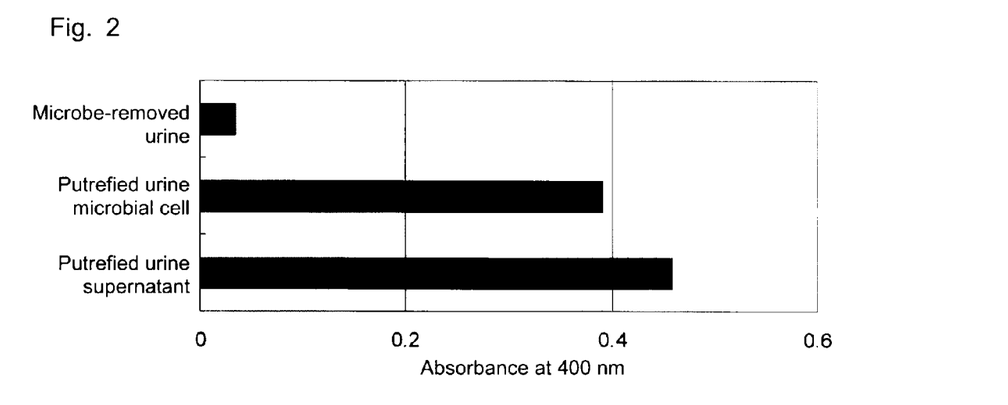
FIG. 2 A graph illustrating the results of measurement of the β-glucuronidase activity of microbe-removed urine, a putrefied urine microbial cell and a putrefied urine supernatant.

The above-mentioned reaction solution immediately after the start of the reaction and after 24 hours of reaction was diluted with a 0.2 M glycine buffer (pH 10.4) and measured for its absorbance at a wavelength of 400 nm. A value obtained by subtracting the absorbance immediately after the start from the absorbance after 24 hours of reaction was used as an index of a β-glucuronidase activity to compare the respective samples. The results of the measurement of the activity are shown in FIG. 2.

The results indicate that, the microbial cells grown in the putrefied urine has β-glucuronidase activity, the supernatant without the microbial cell also has β-glucuronidase activity, and thus an enzyme produced by those microbial cells is secreted to the outside of microbial cells as well.

(3) Sensory Evaluation of Odor of Microbe-Removed Urine and Putrefied Urine

Microbe-removed urine and putrefied urine were subjected to evaluation of odor at the bottle outlet, in the evaluation the bottle used for storage was directly used.

Figure 3:
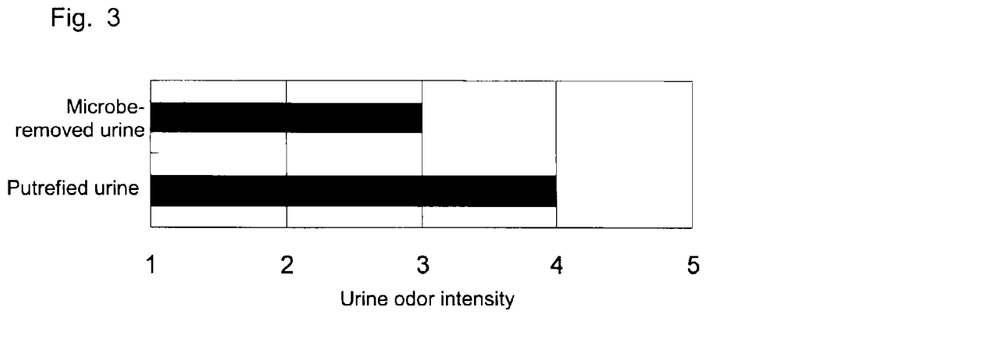
FIG. 3 A graph illustrating the sensory evaluation results of the urine odor intensity of microbe-removed urine and putrefied urine.

Sensory evaluation of odor was performed by six panelists, the evaluation being based on the six-level odor intensity indication method as described in the item (2) of Reference Example 2. The averages of the evaluation by the panelists are shown in FIG. 3.

According to the results, the increase of urine odor intensity by microbial cells that grew in urine was confirmed.

Example 1

Inhibition of β-Glucuronidase Activity with Specific Compound and Plant Extract

100 μL of a 2 mM PNPG aqueous solution, 40 μL of a 0.5 M phosphate buffer (pH 6.8), 38 μL of ion exchanged water and 2 μL of a 10 or 1 wt % dipropylene glycol (DPG) solution of various compounds or plant extracts were mixed in a bottle γ-ray sterilized in advance, and subsequently 20 μL of a β-glucuronidase aqueous solution adjusted to 16 units/mL was added, in order to allow the enzyme to react in a thermostat bath at 37° C. for 2 hours. Further, in the case of some of compounds, in addition to the above steps, the same experiment was performed using a 0.1 wt % DPG solution as well. As a result, the concentrations of the test compounds and plant extracts in the reaction solution were adjusted to 0.1, 0.01 and 0.001 wt %, respectively. Further, a product prepared by adding DPG in place of the above-mentioned compounds and plant extracts was used as a control, and a product prepared by adding ion exchanged water in place of an enzyme solution was used as a blank for each sample and control, and the respective products were allowed to react for 2 hours in the same manner. It should be noted that the plant extract sample was used as a solvent extract.

The above-mentioned reaction solution was diluted with a 0.2 M glycine buffer (pH 10.4) and measured for its absorbance at a wavelength of 400 nm. The relative activity inhibition rate of a β-glucuronidase was determined by using the obtained measurement value in accordance with the following equation. The results are shown in Tables 2a and 2b.

Absorbance change of control=Absorbance of control−Absorbance of blank for each control Absorbance change of sample=Absorbance of sample−Absorbance of blank for each sample Activity inhibition rate (%)=[(Absorbance change of control−Absorbance change of sample)/Absorbance change of control]×100

TABLE 2a

| Component | Classification | Inhibition rate (%) | | |
|---|---|---|---|---|
| | | Concentration 0.1% | Concentration 0.01% | Concentration 0.001% |
| 3-Methyl-4(5)-cyclopentadecen-1-one | Ketone | 98.8 | 99.1 | 92.4 |
| 3-Methylcyclopentadecanone | Ketone | 86.4 | 57.3 | |
| 4-Cyclopentadecen-1-one | Ketone | 99.1 | 93.5 | 67.2 |
| 5-Cyclohexadecen-1-one | Ketone | 98.4 | 93.9 | 65.8 |
| 8-Cyclohexadecen-1-one | Ketone | 100.0 | 99.9 | 95.8 |
| 9-Cycloheptadecen-1-one | Ketone | 100.0 | 96.3 | 95.8 |
| Cyclopentadecanone | Ketone | 73.3 | 35.6 | |
| 2-Pentylcyclopentenone | Ketone | 97.8 | 93.3 | |
| α-Damascone | Ketone | 89.9 | 42.6 | |
| β-Damascone | Ketone | 77.3 | 39.5 | |
| cis-Jasmone | Ketone | 99.2 | 77.2 | 24.8 |
| 2-Heptylcyclopentanone | Ketone | 70.6 | 17.1 | |
| α-Ionone | Ketone | 91.8 | 43.3 | |
| β-Ionone | Ketone | 81.1 | 40.2 | |
| α-Methylionone | Ketone | 91.1 | 57.5 | |
| γ-Methylionone | Ketone | 98.5 | 84.1 | 22.0 |
| Iso E Super | Ketone | 85.9 | 63.1 | |
| Calone | Ketone | 73.3 | 17.3 | |
| Nootkatone | Ketone | 95.2 | 80.8 | |
| 10-Oxa-16-hexadecanolide | Ester | 99.4 | 95.8 | 63.0 |
| 11-Oxa-16-hexadecanolide | Ester | 62.8 | 26.8 | |
| 4(5)-Cyclopentadecenolide | Ester | 76.5 | 47.1 | |
| 7-Cyclohexadecenolide | Ester | 99.6 | 98.5 | 88.1 |
| Citronellyl acetate | Ester | 84.2 | 44.8 | |
| Linalyl acetate | Ester | 95.8 | 62.6 | |
| Terpinyl acetate | Ester | 94.7 | 65.5 | |
| cis-3-Hexenyl benzoate | Ester | 80.6 | 45.1 | |
| Cinnamyl acetate | Ester | 96.2 | 51.3 | |
| Methyl-2-nonynoate | Ester | 98.2 | 95.3 | |
| Anisaldehyde | Aldehyde | 85.9 | 15.3 | |
| Cinnamic aldehyde | Aldehyde | 100.0 | 96.8 | 46.4 |
| Cuminaldehyde | Aldehyde | 97.1 | 37.8 | |
| Cyclamen aldehyde | Aldehyde | 87.5 | 82.7 | 27.4 |
| Ethylvanillin | Aldehyde | 78.5 | 38.5 | |
| Helional | Aldehyde | 76.4 | 32.4 | |
| Lilial | Aldehyde | 72.3 | 60.9 | |
| Phenylacetaldehyde | Aldehyde | 72.2 | 31.9 | |
| 3-Phenylpropanal | Aldehyde | 81.7 | 23.3 | |
| Vanillin | Aldehyde | 82.1 | 49.5 | |
| Dupical | Aldehyde | 73.5 | 65.5 | |
| Ligustral | Aldehyde | 76.2 | 30.1 | |
| Lyral | Aldehyde | 94.4 | 51.6 | |
| Myrac aldehyde | Aldehyde | 63.7 | 49.7 | |
| 2,6-Nonadienal | Aldehyde | 95.2 | 60.9 | |
| Citral | Aldehyde | 84.1 | 29.1 | |
| Hydroxycitronellal | Aldehyde | 85.3 | 24.2 | |
| 2-Methylundecanal | Aldehyde | 62.6 | 57.0 | |

TABLE 2b

| Component | Classification | Inhibition rate (%) | | |
|---|---|---|---|---|
| | | Concentration 0.1% | Concentration 0.01% | Concentration 0.001% |
| Citronellol | Alcohol | 76.2 | 47.4 | |
| Geraniol | Alcohol | 79.8 | 56.8 | |
| Linalool | Alcohol | 91.0 | 31.7 | |
| Linalool oxide | Alcohol | 77.6 | 24.3 | |
| Nerol | Alcohol | 85.7 | 44.0 | |
| Terpineol | Alcohol | 91.7 | 37.6 | |
| Eugenol | Alcohol | 93.2 | 36.8 | |
| Cinnamic alcohol | Alcohol | 93.5 | 56.2 | |
| Phenylhexanol | Alcohol | 61.2 | 52.1 | |
| Vetiverol | Alcohol | 97.1 | 88.0 | |
| p-Cresyl methyl ether | Ether | 85.9 | 24.0 | |
| Estragole | Ether | 99.4 | 94.6 | |
| Grisalva | Ether | 77.3 | 50.4 | |
| Phenylethyl isoamyl ether | Ether | 88.8 | 60.8 | |
| Cedroxide | Ether | 82.6 | 40.1 | |
| Madrox | Ether | 92.4 | 60.9 | |

TABLE 2b-continued

| Component | Classification | Inhibition rate (%) | | |
|---|---|---|---|---|
| | | Concentration 0.1% | Concentration 0.01% | Concentration 0.001% |
| Palisandin | Ether | 85.0 | 53.3 | |
| α-Phellandrene | Terpene | 93.6 | 50.0 | |
| Citronellyl nitrile | Terpene | 92.4 | 41.8 | |
| Galla rhois extract | Plant extract | 97.5 | 90.4 | 6.3 |
| Syzygium aromaticum extract | Plant extract | 79.8 | 13.1 | |
| Hamamelis virginiana extract | Plant extract | 71.5 | 10.2 | |
| D-Glucaro-1,4-lactone | Ester | 98.0 | 80.4 | 31.1 |

The results revealed that the tested compound and plant extract samples have a β-glucuronidase inhibitory activity.

Example 2

Inhibition of β-Glucuronidase Activity Derived from Urine Putrefying Microbial Cell 250 µL of a 2 mM PNPG aqueous solution, 100 µL of a 0.5 M phosphate buffer (pH 6.8), 5 µL of a 10 wt % 8-cyclohexadecen-1-one DPG solution and 100 µL of ion exchanged water were mixed in a bottle γ-ray sterilized in advance, and subsequently 50 µL of the putrefied urine supernatant sample in Reference Example 3 were added. The mixture was allowed to react at room temperature. The concentration of 8-cyclohexadecen-1-one in the reaction solution was 0.01 wt %. Further, a sample without addition of the 8-cyclohexadecen-1-one DPG solution was used as a control and allowed to react as the same.

Figure 4:
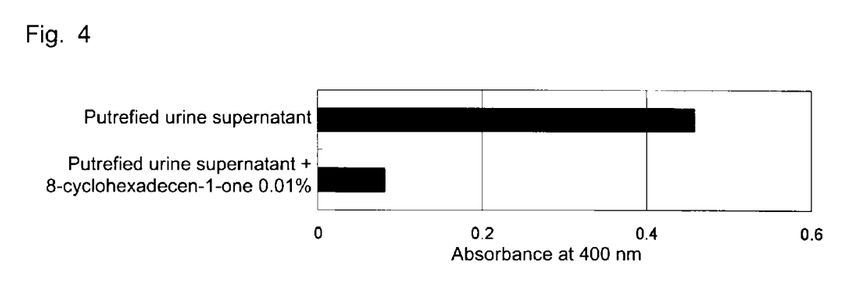
FIG. 4 A graph illustrating the inhibition of β-glucuronidase activity by 8-cyclohexadecen-1-one.

The above-mentioned reaction solution immediately after the start of the reaction and after 24 hours of reaction was diluted with a 0.2 M glycine buffer (pH 10.4) and measured for its absorbance at a wavelength of 400 nm. A value obtained by subtracting the absorbance immediately after the start from the absorbance after 24 hours of reaction was used as an index of a β-glucuronidase activity. The results are shown in FIG. 4.

The results revealed that 8-cyclohexadecen-1-one suppressed the β-glucuronidase activity derived from microbial cells grown in the putrefied urine.

Example 3

Suppression of Production of Volatile Compound from Urine (1) Preparation of Sample 9.9 mL of a human urine sample (a mixture of urine from five humans) which had been subjected to a microbe-removing operation with a 0.2-µm filter immediately after the collection and 10 µL of a 10 wt % 8-cyclohexadecen-1-one DPG solution were added to a bottle γ-ray sterilized in advance, and subsequently 0.1 mL of a α-glucuronidase aqueous solution adjusted to 250 units/mL was added and mixed. The mixture was incubated in a thermostat bath at 25° C. and allowed to react for 22 hours. The concentration of 8-cyclohexadecen-1-one in the reaction solution was 0.01 wt %. Further, a product prepared by adding 0.1 mL of an enzyme solution to 9.9 mL of the microbe-removed urine sample was used as a control, a product prepared by adding 0.1 mL of ion exchanged water to 9.9 mL of the microbe-removed urine sample was used as a blank, and the respective products were allowed to react for 22 hours in the same manner.

After the completion of the reaction, to 9 mL of the reaction solution, a benzyl benzoate ethanol solution was added as an internal standard. The mixture was extracted twice with 10 mL of diethyl ether. The extracted solutions were combined and dried over anhydrous magnesium sulfate. After drying, a solid was separated by filtration, and the filtrate was concentrated with a rotary evaporator to prepare a sample for measurement.

(2) Suppression of Production of Volatile Compound

Measurement was performed with a gas chromatograph mass spectrometer. The production amount of the volatile compound detected was calculated as a peak area ratio with respect to an internal standard. The production suppression rate for each of volatile components was determined by using the obtained value in accordance with the following equation. The results are shown in Table 3.

Production amount of control=Peak area ratio of control—Peak area ratio of blank Production amount of sample=Peak area ratio of sample−Peak area ratio of blank Production suppression rate (%)=[(Production amount of control −Production amount of sample)/Production amount of control]×100

TABLE 3

| Volatile component | Production suppression rate (%) |
|---|---|
| Phenol | 70 |
| p-Cresol | 63 |
| 4-Vinyl-2-methoxyphenol | 55 |
| 4-Vinylphenol | 57 |
| 2-Methoxy-1,3-benzenediol | 73 |
| 1,4-Benzenediol | 73 |
| 1,3-Benzenediol | 100 |
| Indole | 57 |

The results revealed that 8-cyclohexadecen-1-one suppressed the production of all of phenol-based compounds and indole produced from urine by β-glucuronidase activity.

Example 4

Suppression of Generation of Urine Odor (1) Preparation of Sample

360 µL of a human urine sample (a mixture of urine from five humans), which had been subjected to a microbe-removing operation with a 0.2-µm filter immediately after the collection, and 4 µL of a 10 wt % 8-cyclohexadecen-1-one DPG solution were added to a bottle γ-ray sterilized in advance, and subsequently 40 μL of a β-glucuronidase aqueous solution adjusted to 20 units/mL was added and mixed. The mixture was incubated in a thermostat bath at 25° C. and allowed to react for 2 hours. The concentration of 8-cyclohexadecen-1-one in the reaction solution was 0.01 wt %. Further, a product prepared by adding 4 μL of DPG and 40 μL of an enzyme solution to 360 μL of the microbe-removed urine sample and mixing was used as a control, a product prepared by adding 4 μL of DPG and 40 μL of ion exchanged water to 360 μL of the microbe-removed urine sample and mixing was used as a blank, and the respective products were allowed to react for 2 hours in the same manner. An equal amount of the each sample was dropped onto the tip of a smelling strip, and the strip was used as a sample for evaluation.

(2) Confirmation of Urine Odor Suppression by Sensory Evaluation

Figure 5:
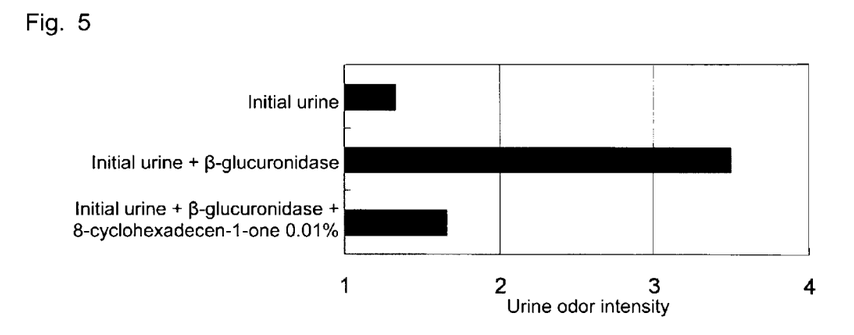
FIG. 5 A graph illustrating the effect for suppressing the urine odor by 8-cyclohexadecen-1-one.

Sensory evaluation of odor was performed by six panelists, the evaluation being based on the six-level odor intensity indication method as described in the item (2) of Reference Example 2. The averages of the evaluation by the panelists are shown in FIG. 5.

The results revealed that 8-cyclohexadecen-1-one also sensuously suppressed the generation of urine odor.

Example 5

Spray Type Composition for Suppressing Generation of Urine Odor

Compositions for suppressing the generation of urine odor (for spray), a to k and 1 to w, each containing the β-glucuronidase inhibitor according to the present invention, and comparative compositions 1 and 2, these composition (wt %) as shown in Tables 4 and 5, were prepared, and filled in a trigger spray bottle.

Each of those compositions was sprayed with the trigger spray bottle onto a tile surface having dimensions of 10 cm by 10 cm in an amount of 0.01 g/cm² and dried for 1 day. After that, 0.5 g of human urine (a mixture of urine from five humans) was uniformly applied thereto and dried for 12 hours. The urine odor intensity after drying was evaluated based on the six-level odor intensity indication method as described in the item (2) of Reference Example 2. Tables 4 and 5 each shows the most popular evaluation in evaluation scores for the urine odor intensity by three panelists. The results confirmed that the composition containing the β-glucuronidase inhibitor of the present invention had an effect of suppressing the generation of urine odor.

TABLE 4

| Component | Composition for suppressing generation of urine odor (for spray) (wt %) | | | | | | | | | | | |
|---|---|---|---|---|---|---|---|---|---|---|---|---|
| | a | b | c | d | e | f | g | h | i | j | k | Comp 1 |
| 9-Cycloheptadecen-1-one | 0.1 | | | | | | | | | | 0.01 | |
| 8-Cyclohexadecen-1-one | | 0.1 | | | | | | | | | 0.01 | |
| Estragole | | | 0.2 | | | | | | | | 0.02 | |
| Cinnamic aldehyde | | | | 0.2 | | | | | | | 0.02 | |
| Methyl-2-nonynoate | | | | | 0.2 | | | | | | 0.02 | |
| Vetiverol | | | | | | 0.5 | | | | | 0.05 | |
| Cyclamen aldehyde | | | | | | | 0.5 | | | | 0.05 | |
| γ-Methylionone | | | | | | | | 0.5 | | | 0.05 | |
| cis-Jasmone | | | | | | | | | 0.5 | | 0.1 | |
| Nootkatone | | | | | | | | | | 0.5 | 0.1 | |
| Green tea extract | 0.5 | 0.5 | 0.5 | 0.5 | 0.5 | 0.5 | 0.5 | 0.5 | 0.5 | 0.5 | 0.5 | 0.5 |
| Propylene glycol | 5 | 5 | 5 | 5 | 5 | 5 | 5 | 5 | 5 | 5 | 5 | 5 |
| Ethanol | 5 | 5 | 5 | 5 | 5 | 5 | 5 | 5 | 5 | 5 | 5 | 5 |
| Water | Balance | Balance | Balance | Balance | Balance | Balance | Balance | Balance | Balance | Balance | Balance | Balance |
| <Urine odor intensity> | 2 | 2 | 2 | 2 | 2 | 2 | 2 | 2 | 2 | 2 | 2 | 3.5 |

TABLE 5

| Component | Composition for suppressing generation of urine odor (for spray) (wt %) | | | | | | | | | | | |
|---|---|---|---|---|---|---|---|---|---|---|---|---|
| | l | m | n | o | p | q | r | s | t | u | v | w | Comp 2 |
| 9-Cycloheptadecen-1-one | 0.1 | | | | | | | | | | | 0.01 | |
| 8-Cyclohexadecen-1-one | | 0.1 | | | | | | | | | | 0.01 | |
| 7-Cyclohexadecenolide | | | 0.1 | | | | | | | | | 0.02 | |
| Estragole | | | | 0.2 | | | | | | | | 0.02 | |
| Cinnamic aldehyde | | | | | 0.2 | | | | | | | 0.02 | |
| Methyl-2-nonynoate | | | | | | 0.2 | | | | | | 0.02 | |
| Vetiverol | | | | | | | 0.5 | | | | | 0.05 | |
| Cyclamen aldehyde | | | | | | | | 0.5 | | | | 0.05 | |
| γ-Methylionone | | | | | | | | | 0.5 | | | 0.05 | |
| cis-Jasmone | | | | | | | | | | 0.5 | | 0.1 | |
| Nootkatone | | | | | | | | | | | 0.5 | 0.1 | |
| Ethanol | 50 | 50 | 50 | 50 | 50 | 50 | 50 | 50 | 50 | 50 | 50 | 50 | 50 |
| Water | Balance | Balance | Balance | Balance | Balance | Balance | Balance | Balance | Balance | Balance | Balance | Balance | Balance |
| <Urine odor intensity> | 2.5 | 2.5 | 2.5 | 2 | 2 | 2 | 2 | 2 | 2 | 2 | 2 | 2 | 4 |

Example 6

Disposable Diaper

A composition for suppressing the generation of urine odor containing the β-glucuronidase inhibitor according to the present invention, the composition (wt %) being as shown in Table 6, was prepared. The composition was sprayed onto ground paper for a disposable diaper (basis weight: 16 g/m$^2$) and dried. After that, a product prepared by uniformly mixing 100 parts by weight of flap pulp and 100 parts by weight of a water-absorbent polymer (a polyacrylic acid crosslinked product) was packed with the ground paper, to obtain an absorber. The basis weight of a flap pulp/water-absorbent polymer mixed product in the absorber was 300 g/m$^2$. The prepared absorber was used to prepare a disposable diaper. The amount of the β-glucuronidase inhibitor in the composition for suppressing the generation of urine odor, sprayed onto the ground paper, was 0.32 g/m$^2$ of ground paper.

of urine odor even after 24 hours, compared to the blank. Further, an effect for suppressing the increase of urine odor by 8-cyclohexadecen-1-one had, even after 48 hours, was confirmed.

TABLE 7

| β-Glucuronidase inhibitor | Urine odor intensity | | |
| --- | --- | --- | --- |
| | After 1 hour | After 24 hours | After 48 hours |
| Blank (containing no β-Glucuronidase inhibitor) | 1.6 | 2.9 | 3.9 |
| 8-Cyclohexadecen-1-one | 1.3 | 1.5 | 1.9 |
| D-Glucaro-1,4-lactone | 1.6 | 1.9 | 3.3 |
| *Galla rhois* extract | 1.7 | 1.6 | 3.1 |

TABLE 6

| Component | Composition for suppressing generation of urine odor (wt %) | | | | | | | | | |
| --- | --- | --- | --- | --- | --- | --- | --- | --- | --- | --- |
| | a1 | b1 | c1 | d1 | e1 | f1 | g1 | h1 | i1 | j1 |
| 9-Cycloheptadecen-1-one | 1 | | | | | | | | | 0.1 |
| 8-Cyclohexadecen-1-one | | 1 | | | | | | | | 0.1 |
| 7-Cyclohexadecenolide | | | 1 | | | | | | | 0.1 |
| 3-Methyl-4(5)-cyclopentadecen-1-one | | | | 1 | | | | | | 0.1 |
| 4-Cyclopentadecen-1-one | | | | | 1 | | | | | 0.1 |
| 10-Oxa-16-hexadecanolide | | | | | | 2 | | | | 0.2 |
| D-Glucaro-1,4-lactone | | | | | | | 3 | | | 0.3 |
| Galla rhois extract | | | | | | | | 5 | | 0.4 |
| *Hamamelis virginiana* extract | | | | | | | | | 10 | 1.0 |
| Dipropylene glycol (DPG) | 5 | 5 | 5 | 5 | 5 | 5 | 5 | 5 | 5 | 5 |
| Ethanol | Balance | Balance | Balance | Balance | Balance | Balance | Balance | Balance | Balance | Balance |

Example 7

Urine Catching Pad

A urine catching pad containing the β-glucuronidase inhibitor of the present invention as shown in Table 7 was prepared. Specifically, the urine catching pad was prepared by replacing only a water-absorbent polymer in the commercially available urine catching pad "Relief urine catching pad safe absorption (Anshin-Kyusyu)" (manufactured by Kao Corporation) with a water-absorbent polymer wherein the β-glucuronidase inhibitor of the present invention was added. The added amount of the inhibitor to the water-absorbent polymer was 1 wt. % with respect to the water-absorbent polymer, and was equivalent to 1.5 g/m$^2$ with respect to the urine catching pad.

A urine addition test was performed by using test pieces having dimensions of 19 cm by 7 cm being cut out from the urine catching pad, and using a test piece containing no β-glucuronidase inhibitor as a blank. The test was performed as follows: 30 g of human urine (a mixture of urine from five humans) were added to these test pieces cut out from the urine catching pad, and the urine odor intensity after 1 hour, after 24 hours, and after 48 hours under preservation at 30° C. was evaluated by five panelists based on the six-level odor intensity indication method as described in the item (2) of Reference Example 2. The average values of the urine odor intensity evaluation after each period of time are shown in Table 7.

As shown in Table 7, a test piece of the urine catching pad containing the β-glucuronidase inhibitor of the present invention was found to have an effect for suppressing the increase

The invention claimed is:

1. A method of suppressing generation of urine odor, comprising: applying a β-glucuronidase inhibitor to an object before urine is deposited to the object or before urine is dried after having been deposited to the object wherein the β-glucuronidase inhibitor comprises at least one macrocyclic ketone selected from the group consisting of 3-methyl-4(5)-cyclopentadecen-1-one, 4-cyclopentadecen-1-one, 5-cyclohexadecen-1-one, 8-cyclohexadecen-1-one, 9-cycloheptadecen-1-one, and 3-methylcyclopentadecanone.

2. A method of inhibiting β-glucuronidase, comprising applying a β-glucuronidase inhibitor to an object, a subject, or a sample,
   wherein
   (i) the object, the subject, or the sample to which the β-glucuronidase inhibitor has been applied comprises β-glucuronidase,
   (ii) β-glucuronidase is added to the object, the subject, or the sample prior, during and/or after the applying the β-glucuronidase inhibitor, and/or
   (iii) β-glucuronidase is generated in or on the object, the subject, or the sample prior, during and/or after the applying the β-glucuronidase inhibitor,
   wherein the β-glucuronidase inhibitor comprises at least one member selected from the group consisting of 3-methyl-4(5)-cyclopentadecen-1-one, 4-cyclopentadecen-1-one, 5-cyclohexadecen-1-one, 8-cyclohexadecen-1-one, 3-methylcyclopentadecanone, and 9-cycloheptadecen-1-one, and the β-glucuronidase inhibitor is applied at the concentration of from 0.001 to 1 wt. %.

3. The method according to claim 2, wherein the β-glucuronidase inhibitor is applied to an object before urine is deposited to the object or before urine is dried after having been deposited to the object.

4. The method according to claim 2, wherein the β-glucuronidase inhibitor is applied to an environmental hygiene product or a sanitary product.

5. The method according to claim 2, wherein the β-glucuronidase is added to the object, the subject, or the sample prior or during the application of the β-glucuronidase inhibitor.

6. The method according to claim 2, wherein the β-glucuronidase inhibitor comprises at least one member selected from the group consisting of 8-cyclohexadecen-1-one and 9-cycloheptadecen-1-one.

7. The method according to claim 2, wherein the β-glucuronidase inhibitor is applied at the concentration of from 0.005 to 0.5 wt. %.

8. The method according to claim 2, wherein an inhibition rate of the β-glucuronidase inhibitor is at least 95% at the concentration of the β-glucuronidase inhibitor of 0.001%.

9. The method according to claim 2, wherein an inhibition rate of the β-glucuronidase inhibitor is greater than 96% at the concentration of the β-glucuronidase inhibitor of 0.01%.

* * * * *